Figure 1:
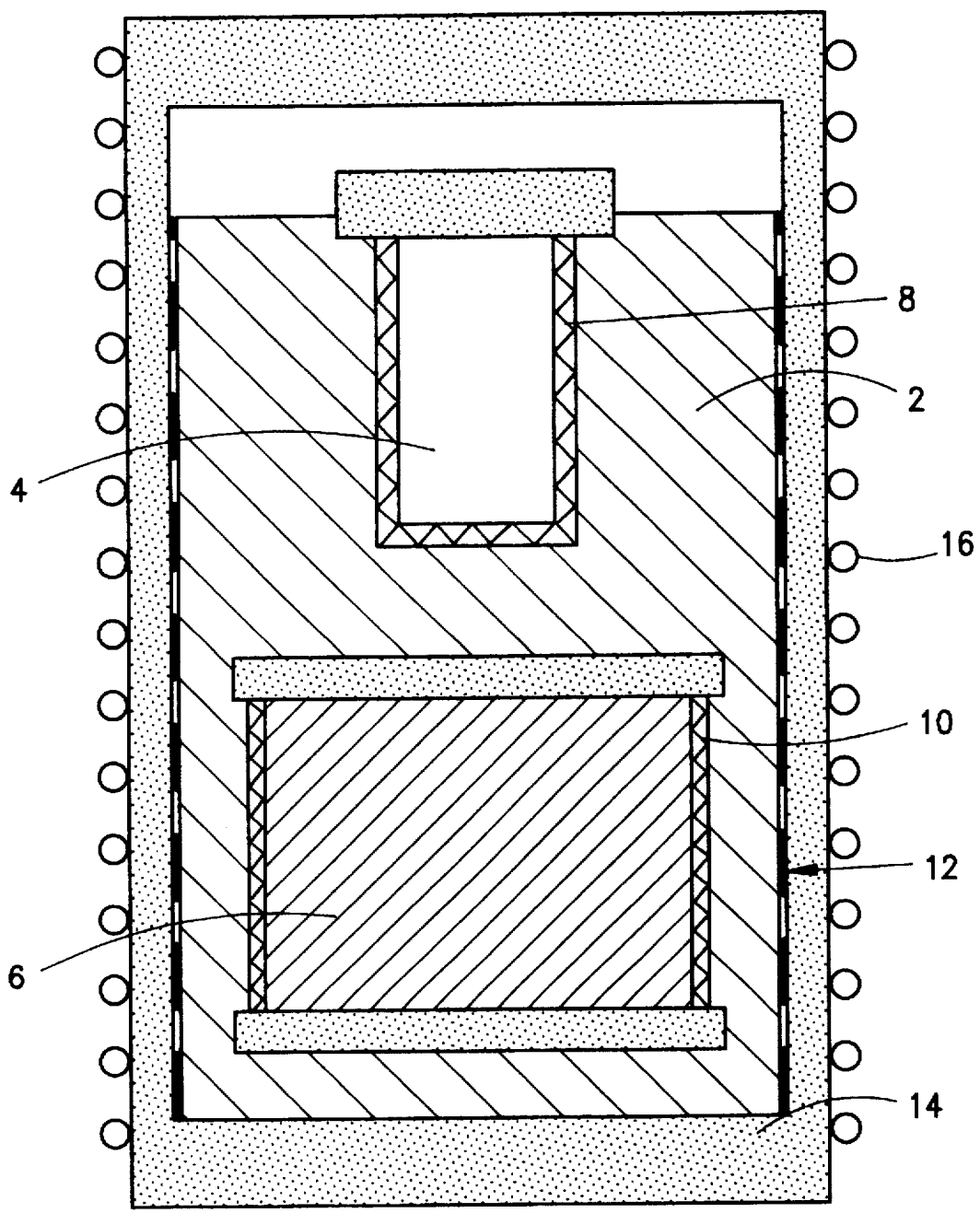

United States Patent [19]

Hemmerich et al.

[11] Patent Number: 5,741,068
[45] Date of Patent: Apr. 21, 1998

[54] TEMPERATURE DERIVATIVE SENSING AND REGULATING DEVICE AND METHOD

[75] Inventors: Johann Ludwig Hemmerich, Oxford; Paul Milverton, Oxon, both of United Kingdom; Luigi Serio, Putignano, Italy

[73] Assignee: European Atomic Energy Community (Euratom), Plateau Du Kirchberg, Luxembourg

[21] Appl. No.: 583,011

[22] PCT Filed: Jul. 21, 1994

[86] PCT No.: PCT/EP94/02414

§ 371 Date: Jan. 29, 1996

§ 102(e) Date: Jan. 29, 1996

[87] PCT Pub. No.: WO95/04317

PCT Pub. Date: Feb. 9, 1995

[30] Foreign Application Priority Data

Jul. 29, 1993 [GB] United Kingdom ............ 9315687

[51] Int. Cl.⁶ .................................................. G01K 17/00
[52] U.S. Cl. ................................................................ 374/31
[58] Field of Search ................................. 374/29, 30, 31, 374/32, 33, 39

[56] References Cited

U.S. PATENT DOCUMENTS

| | | | |
|---|---|---|---|
| 3,372,588 | 3/1968 | Ziemke et al. | 374/29 |
| 3,542,123 | 11/1970 | Hornbaker et al. | 374/30 X |
| 3,715,923 | 2/1973 | Hornbaker et al. | 374/30 X |
| 3,720,103 | 3/1973 | Adams et al. | 374/29 |
| 4,274,475 | 6/1981 | Rall et al. | 374/29 X |

FOREIGN PATENT DOCUMENTS

A-570 613   12/1975   Switzerland.

OTHER PUBLICATIONS

*Soviet Inventions Illustrated*, X section, week 34, issued Sep. 29, 1976.
*Soviet Inventions Illustrated*, R section, week 20, issued Jun. 27, 1978.
*Soviet Inventions Illustrated*, A-M section, week 9241, issued Nov. 25, 1992.
*Soviet Inventions Illustrated*, E section, week 9250, issued Feb. 3, 1993.

*Primary Examiner*—George M. Dombroske
*Assistant Examiner*—Paul D. Amrozowicz
*Attorney, Agent, or Firm*—Bacon & Thomas

[57] ABSTRACT

A temperature derivative sensing and regulating device and method is described which facilitates the maintainance of a very stable isothermal environment for an item, apparatus or facility or a constant rate of temperarture change. The device comprises a block of material having no internal heat sources, a thermal conductivity greater than 100 $Wm^1K^{-1}$ and a specific heat capacity greater than 385 $JK^{-1}kg^{-1}$. The block is surrounded by means for measuring the heat flow to and from the block and the device is further provided with means for generating a signal proportional to said heat flow and means for interfacing with the controller of a heating or cooling means associated with the item, apparatus or facility.

15 Claims, 2 Drawing Sheets

TEMPERATURE DERIVATIVE SENSING AND REGULATING DEVICE AND METHOD

The invention relates to a thermostatic device and to a method of sensing and regulating the temperature of an item, article or facility using said device. The invention may be applied in a variety of circumstances where accurate temperature regulation is required, particularly to sustain an isothermal environment or to control the rate of temperature change. It has been found especially suitable for use in the field of thermoelectric calorimetry the discussion of which will be used to exemplify the invention.

Devices and methods have been known for many years which permit sensing and regulation of temperature, either to maintain an environment or article at a particular temperature or to control the rate of temperature change. Thermostatic control of temperature is applied to everyday items and systems such as ovens, refrigerators and central heating systems as well as more sophisticated equipment in laboratories or factories. For many applications, small variations from the isothermal state or from the desired rate of temperature change can be tolerated so that fairly crude thermostatic devices and temperature control systems can be used. However there are cases where temperature must be regulated much more precisely.

One area where this is the case is in the field of thermoelectric calorimetry where it is desired to measure the heat generated from an article or material, for example a mechanical, electrical or electronic device, chemical or biochemical reaction or radioactive isotope. The calorimeter may be required to measure very small heat fluxes, as low as 10 2 mW. In such circumstances it has been found that conventional arrangements for thermostatic control are not adequate because the magnitude of the temperature drifts from an absolutely stable isothermal state cause errors in the signals which may be larger than heat fluxes being measured. There has thus arisen the need for much improved thermostatic control in such applications. Further the physical principles underlying the device and method of the invention can be best exemplified when considering thermoelectric calorimetry.

Thermoelectric calorimetry is governed by the general heat conduction equation as follows:

$$\Delta = \Pi + \Sigma \qquad (1)$$

where $\Delta$ represents the total energy increase in the volume V of the calorimeter per unit time, $\Pi$ represents the total heat flow into the volume through the closed surface area A of the volume and $\Sigma$ is the quantity of interest i.e. the sum of all heat generating sources contained in the volume.

The heat generated by an article or material in a calorimeter may be measured by the adiabatic method or the thermostatic method. In the adiabatic method a calorimeter body of known heat capacity is, ideally, thermally insulated in such a way that any heat flow $\Pi$ through its surface is zero. In this case the following equation applies:

$$\Sigma = C_c \cdot \dot{\Theta} \qquad (2)$$

where $C_c$ is the heat capacity of the calorimeter body and $\dot{\Theta}$ is the change in temperature with time or $d\Theta/dt$ hereinafter referred to as the temperature derivative. Thus the heat generated by the sample $\Sigma$ can be obtained provided $C_c$ and $\dot{\Theta}$ can be measured sufficiently accurately. However problems arise with this method where a small heat source in a volume of large heat capacity gives rise to a temperature rise rate which is smaller than can be accurately measured. The most accurate methods available will measure only to $\pm 1 \times 10^{-3} \text{kh}^{-1}$.

In the thermostatic method the calorimeter body containing the heat source is placed in a temperature stabilized environment. Its surface A is covered by a heat flow sensing device (e.g. thermopile) which measures the (integrated) heat flow $\Pi$, as given in equation (1), through the total surface A.

Ideally, the environment is thermostatically controlled to the extent that, once equilibrium is established, all the temperature derivatives with respect to time become negligibly small so that:

$$\Sigma = -\Pi \qquad (3)$$

However, the above represents the ideal situation and in practice, because of the limitations on temperature control, $$\Sigma = -\Pi + C_c \cdot \dot{\Theta} \qquad (4)$$

where drifts $\pm \dot{\Theta}$ in the thermostatic control cause an error signal $$\Delta = +C_c \dot{\Theta} \qquad (5)$$

is proportional to both $\dot{\Theta}$ and the total calorimeter volume heat capacity $C_c$.

Presently used thermostats allow control of $\dot{\Theta}$ to $\pm 1 \times 10^{-2}$ (at best $\pm 1 \times 10^{-3}$)kh$^{-1}$ which is not adequate for the measurement of very low levels of heat generation from a sample.

In the past attempts have been made to overcome the problems of poor thermostatic control in calorimetry by using the so-called "double-cup" or twin calorimeters which comprise two identical calorimeter chambers with identical heat capacity, source distribution and sensors. One chamber contains the unknown sample to be measured and the other has an electrical heater with accurately measurable power. Therefore the heat capacity effects and thus the drift term $\Delta$ is cancelled out. However these devices are still affected by imperfections in symmetry and their performance would be substantially enhanced by improvements in thermostatic control.

The present inventors have developed a new thermostatic device and method which overcomes the aforementioned problems in thermoelectric calorimetry but is equally suitable for temperature sensing and regulation in other technical applications as will be discussed below.

A temperature derivative sensing and regulating device in accordance with the invention comprises an inertial mass of material having no internal heat sources, a thermal conductivity greater than 100 Wm$^{-1}$K$^{-1}$ and a specific heat capacity of 385JK$^{-1}$Kg$^{-1}$ or greater, means surrounding said inertial mass for conducting the flow of heat to and from said inertial mass, the heat flow $\Pi_i$ being proportional to the temperature derivative $\dot{\Theta}$ in accordance with the equation $\Pi_i = \dot{\Theta} C_i$ when $C_i$ is the heat capacity of the inertial mass, means for generating a signal proportional to said heat flow and means for interfacing with the controller of a heating or cooling means associated with an item, apparatus or facility whose temperature is to be regulated.

In the application to calorimetry the introduction of an inertial mass with large heat capacity e.g. greater than 2000JK$^{-1}$, into the active volume of a calorimeter results in a heat flow equation:

$$\Pi_i = \dot{\Theta} C_i \qquad (6)$$

when there is no other heat source in the calorimeter, $C_i$ being the heat capacity of the block. Thus in a calorimeter fitted with such an arrangement it is possible to measure $\dot{\Theta}$ with the same sensitivity as the calorimeter signal. Furthermore the temperature can be controlled such that $\dot{\Theta}=0$ as indicated by a heat flow signal $\Pi=0$. As a consequence, the error in measuring $\Sigma$ is always smaller than $\dot{\Theta}C_i$ provided that the heat capacity $C_c$ is smaller than the heat capacity $C_i$ of the inertial mass.

The presence of any heat flow to or from the block as detected by the heat flow measuring means is an indication that the temperature is not constant. All the while the signal from the heat flow measuring means is zero, accurate measurement of the heat generated by any sample in the calorimeter chamber can be made.

An essential feature of the present invention is the provision of an inertial mass or block of high heat capacity, preferably in the range from $2kJK^{-1}$ to $10kJK^{-1}$ with a means for measuring heat flow surrounding it. Metals are the most suitable materials for the inertial mass, especially those with high thermal conductivity such as copper or aluminium.

A suitable means which can surround the block for measuring heat flow is a structure known as a thermopile. This consists of thousands of thermocouple junctions, one set being in contact with the inertial mass wall and one set being in contact with an outer housing or body. As heat flows through the thermopile a temperature difference is established between both sets of thermopile junctions thus generating a voltage which is directly proportional to heat flow. The signal generated by the thermopile can then be fed to the controller of any heating and cooling means which may counteract the temperature change so that $\dot{\Theta}=0$. Because of the very large heat capacity of the inertial mass, once it has equilibrated at the particular temperature it is desired to be maintained, no heat will flow to or from it and the thermopile thus gives a zero voltage reading, but once the temperature drifts from the set point heat flow will occur thus generating an electrical signal.

Apart from its application to calorimetry as discussed above, the temperature derivative sensing and regulating device in accordance with the invention can be used in a variety of other situations where it is desired to maintain a stable isothermal environment. For example it may be applied directly to enhance the performance of temperature sensitive devices such as quartz oscillators for clock applications. Frequency stability in such devices is highly desired for accuracy and this is related directly to temperature stability. Thus by providing a much improved thermal stability the performance of a relatively cheap device may be enhanced to approach the performance of a more expensive one e.g. a cesium clock, used as a frequency or time standard.

Another application of the device in accordance with the invention is to enhance the performance of conventional laboratory or industrial thermostats which are used in process temperature control. In many cases a steady temperature for the process is maintained by means of an internally or externally recirculating heat transfer medium e.g. water, silicone oils or alcohols etc., depending on the process temperature and by use of conventional heaters, coolers, temperature sensors and recirculation pumps. The temperature variation of the process environment thus achieved is typically of the order of $\dot{\Theta}\pm 0.02Kh^{-1}$ but by including a device in accordance with the invention the temperature stability can be substantially improved to a variation of $\pm 1\times 10^{-5}Kh^{-1}$ or better, depending on size of the inertial mass and the sensitivity of the thermopile selected.

Finally, it will of course be appreciated that the invention provides a means of facilitating a change in temperature at constant rate. The signal from the thermopile is proportional to the temperature derivative $\dot{\Theta}$, which is the change of temperature with time. Thus a feedback controller set point can be selected whereby the signal from the thermopile and hence $\dot{\Theta}$ is always kept constant but is not zero i.e. the rate of change of temperature($\dot{\Theta}$) is constant and the resulting temperature ramp linearity is equal to the temperature stability achieved in constant temperature ($\dot{\Theta}=0$).

In another aspect the invention provides a method of measuring the temperature derivative of an item, apparatus or other facility which comprises the steps of:

(a) positioning in the vicinity of said item, apparatus or facility, a device as described above (b) measuring the heat flow to and from the inertial mass as a direct indication of the temperature derivative of said item, (c) converting said measured heat flow into an electrical signal and (d) using said signal to instruct the controller of any heating and cooling means associated with said item apparatus or facility to maintain the temperature derivative at a constant value.

The electrical signal generated is used as part of a feedback control system for regulating temperature, either so that it remains constant or so that it rises or falls at a constant rate. The signal is thus used to instruct the controller of any heating or cooling means associated with said item, apparatus or facility to restore $\dot{\Theta}$ to the desired value. For example where the method of the invention is used to maintain a very stable isothermal environment, adjustment via the feedback system should restore $\dot{\Theta}$ and hence the rate of change of temperature to zero. However if a linear rate of change of temperature is required the set value for $\dot{\Theta}$ will not be zero but will nevertheless be constant.

In yet another aspect the invention provides a method of improving the thermostatic control of a calorimeter or any heat sensitive item or process which method comprises introducing into said calorimeter, a device as described above.

In the case where the method is applied to a thermoelectric calorimeter or quartz oscillator as aforementioned, the block and the surrounding thermopile are disposed in the same body or housing as the calorimeter chamber or oscillator.

In a method in which the device of the invention is used to enhance the performance of a conventional laboratory or industrial thermostat the new device can be inserted between a standard thermostat and the process or test device which is to be maintained at a stable temperature by means of a heat transfer fluid. The heat transfer fluid from the industrial thermostat ($\dot{\Theta}$)$0.02Kh^{-1}$) flows through an additional heating and cooling device, through the device in accordance with the invention, then to the process or test device and finally returns to the industrial thermostat. The means for detecting heat flow in the device of the invention indicates any temperature fluctuation and compensates it by means of the auxilliary heater and/or cooler. Temperature fluctuations and drifts at the exit of the conventional thermostat are thereby suppressed and the process or test device can be supplied with heat transfer fluid of greatly improved temperature stability.

Figure 2:
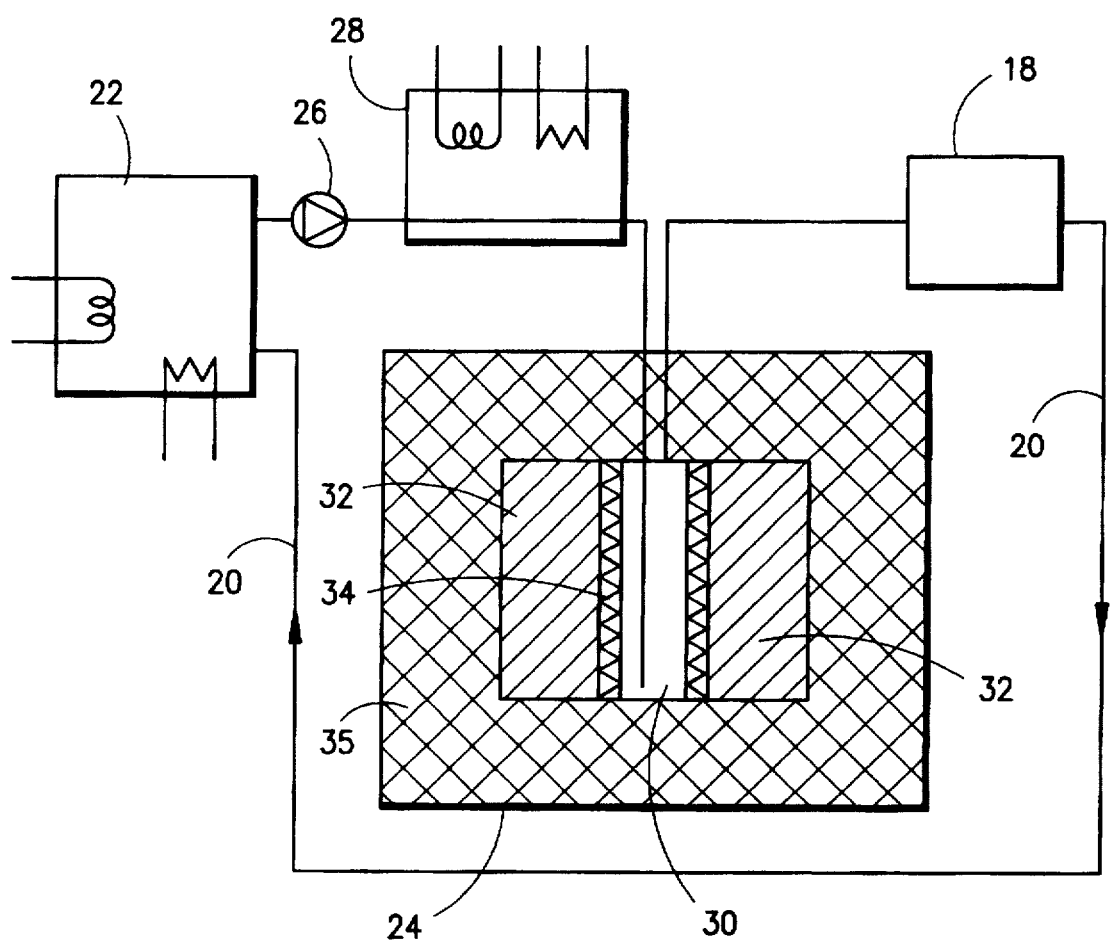

The invention will now be described by way of example with reference to the accompanying drawings in which:

FIG. 1 is a vertical cross-section through a calorimeter fitted with a device in accordance with the invention and FIG. 2 is a circuit diagram of an industrial process where temperature is controlled by a heat transfer fluid and including a device in accordance with the invention.

In FIG. 1 the calorimeter body 2 surrounds the calorimeter chamber 4 and the aluminium block (inertial mass) 6. Both the chamber 4 and the block 6 are surrounded by thermopiles 8 and 10 respectively which generate voltage signals independently of one another. The calorimeter body 2 is surrounded by a heater 12 which is controlled by the signal from the thermopile 10. The entire apparatus is surrounded by thermal insulation 14 and provided with a more conventional external thermostat 16.

In operation the calorimeter is brought to a state of thermal equilibrium and adjusted so that the voltage signal from the thermopile 10 is zero. The sample for testing is introduced into the calorimeter chamber 4 and the calorimeter re-equilibrated until the signal from the thermopile 10 is again 0. The voltage signal from the thermopile 8 is then an accurate measure of the heat generated by the sample.

Standard, commercially available calorimeters can be adapted to include the temperature sensing and regulation device of the current invention. For example the temperature of a calorimeter can be controlled to a stability of $\dot{\Theta} < 1.7 \times 10^{-5} Kh^{-1}$ using a block with a heat capacity of $2200 JK^{-1}$ and using a microvoltmeter. Such stability is sufficient to achieve an accuracy of heat flow measurement down to 100 nW for a differential calorimeter with a heat capacity imbalance of $200 JK^{-1}$.

With more sensitive equipment, for example a calorimeter with a 0.1V/W output signal, a nanovoltmeter with a 10 nV resolution and stability and an inertial mass (e.g. 6.7 Kg Al) with a heat capacity of $6000 JK^{-1}$, it is expected that:

$$\dot{\Theta} = \frac{10 \times 10^{-9}}{0.1 \times 6000} = 1.7 \times 10^{-11} Ks^{-1}$$

or $$\dot{\Theta} = 6 \times 10^{-8} Kh^{-1}$$

In FIG. 2, the temperature of the process 18 is maintained substantially constant by circulation of a heat transfer fluid 20. The temperature of the heat transfer fluid is stabilized by a conventional thermostat 22 and a temperature stabilizing device in accordance with the invention 24 which is fitted in the circuit between the thermostat 22 and the process 18. The circuit is provided with a pump 26 and an auxilliary heating and cooling means 28 between the thermostat 22 and the device 24. The device 24 comprises a central portion 30 through which the heat transfer fluid 20 flows, an inertial mass 32 of a material with high specific heat capacity and high thermal conductivity, a thermopile 34 and thermal insulation 35.

When the process is in operation the heat transfer fluid from the thermostat 22 flows through auxilliary heating and cooling device 28 to the process 18 via the device 24. It then returns to the thermostat 22. The thermopile 34 produces an electrical signal which is proportional to any heat flow to and from the inertial mass 32 and if there is any temperature fluctuation it is compensated for by means of the auxilliary heater or cooler 28.

We claim:

1. A temperature derivative sensing and regulating device to be used with a heat sensitive item, and which comprises an inertial mass of material having no internal heat sources, a thermal conductivity greater than 100 $Wm^{-1}K^{-1}$ and a specific heat capacity of $385 JK^{-1}kg^{-1}$ or greater, and a high heat capacity which is greater than the heat capacity of the heat sensitive item, means surrounding said inertial mass for conducting the flow of heat to and from said inertial mass, the heat flow $\Pi_i$ being proportional to the temperature derivative $\dot{\Theta}$ in accordance with the equation $$\Pi_i = \dot{\Theta} C_i$$

where $C_i$ is the heat capacity of the inertial mass, means for generating a signal proportional to said heat flow and means for interfacing with the controller of a heating or cooling means associated with an item, apparatus or other facility whose temperature is to be regulated.

2. A device as claimed in claim 1 wherein the heat capacity of the inertial mass is in the range from $2kJK^{-1}$ to $10kJK^{-1}$.

3. A device as claimed in claim 1 wherein the inertial mass comprises aluminium or copper.

4. A device as claimed in claim 1 wherein the means surrounding the inertial mass for conducting the flow of heat to and from the inertial mass and for generating a signal proportional to said heat flow is a thermopile.

5. A device as claimed in claim 1 wherein said signal proportional to heat flow is an electrical signal.

6. A device as claimed in claim 1 wherein said signal instructs the said heating and cooling means to heat or cool the item, apparatus or facility to a predetermined set temperature change rate.

7. A device as claimed in claim 1 in combination with a heat sensitive item wherein said inertial mass and said item are disposed in a common housing made of a heat sink material.

8. A device as claimed in claim 7 wherein said item is a thermoelectric calorimeter or a quartz oscillator.

9. A device as claimed in claim 1 wherein the heat sensitive item is a calorimeter or a quartz oscillator.

10. A method of measuring the temperature derivative of an item, apparatus or other facility which comprises the steps of:
 (a) positioning in the vicinity of said item, apparatus or facility a device a according to any preceding claim,
 (b) measuring the heat flow to and from the inertial mass as a direct indication of the temperature derivative of said item, apparatus or other facility,
 (c) converting said measured heat flow into an electrical signal and
 (d) using said signal to instruct the controller of any heating and cooling means associated with said item, apparatus or facility to maintain the temperature derivative at a constant value.

11. A method as claimed in claim 10 which comprises the further step of using said signal to instruct the controller of any heating and cooling means associated with said item, apparatus or facility to adjust the temperature derivative to zero.

12. A method as claimed in claim 10 wherein the heat capacity of said inertial mass is in the range from $2kJK^{-1}$ to $10kJK^{-1}$.

13. A method as claimed in claim 10 wherein said inertial mass comprises aluminium or copper.

14. A method as claimed in claim 10 wherein the means for measuring the flow of heat to and from the inertial mass and for converting said heat flow into an electrical signal is a thermopile.

15. A method of improving the temperature control of a calorimeter or any heat sensitive item or process which comprises the steps of:
 (a) introducing into said item an inertial mass surrounded by a detector of heat flow to and from said mass, said inertial mass having a high heat capacity $C_i$ which is greater than the heat capacity of the calorimeter or the heat sensitive item or process,
 (b) detecting and measuring the heat flow to and from said inertial mass, the heat flow being a direct indication of the temperature derivative $\dot{\Theta}$ in accordance with the equation:

$$\Pi_i = \dot{\Theta} C_i$$

(c) converting the measured flow into an electrical signal and
 (d) using said signal to instruct the controller of any heating and cooling means associated with said calorimeter or any heat sensitive item-or process to operate to restore the heat flow signal $\Pi_i$ and hence $\dot{\Theta}$ to zero or other constant value.

* * * * *